United States Patent
Davis

(10) Patent No.: US 8,561,605 B2
(45) Date of Patent: Oct. 22, 2013

(54) ATRAUMATIC INTRODUCER FOR NASAL ENDOTRACHEAL TUBES AND ITS METHOD OF USE

(76) Inventor: John J. Davis, Troutville, VA (US)

(*) Notice: Subject to any disclaimer, the term of this patent is extended or adjusted under 35 U.S.C. 154(b) by 898 days.

(21) Appl. No.: 12/530,668

(22) PCT Filed: Apr. 10, 2008

(86) PCT No.: PCT/US2008/059946
§ 371 (c)(1),
(2), (4) Date: Sep. 10, 2009

(87) PCT Pub. No.: WO2008/127994
PCT Pub. Date: Oct. 23, 2008

(65) Prior Publication Data
US 2010/0083957 A1    Apr. 8, 2010

Related U.S. Application Data

(60) Provisional application No. 60/911,168, filed on Apr. 11, 2007.

(51) Int. Cl.
*A61M 16/00*    (2006.01)

(52) U.S. Cl.
USPC ............. 128/200.25; 128/207.14; 128/207.18

(58) Field of Classification Search
USPC ............. 128/200.26, 207.14–207.16, 207.29, 128/207.18, 207.21, 200.11, 206.29, 128/206.21; 604/530, 170.01–170.03, 604/164.01–164.05; 600/585, 120
See application file for complete search history.

(56) References Cited

U.S. PATENT DOCUMENTS

| 3,683,908 | A | * | 8/1972 | Michael et al. | ........... 128/207.15 |
| 4,175,564 | A |   | 11/1979 | Kwak | |
| 4,195,624 | A | * | 4/1980 | Douglas | ........................ 600/114 |
| 4,211,234 | A | * | 7/1980 | Fisher | ...................... 128/200.26 |

(Continued)

FOREIGN PATENT DOCUMENTS

JP    61013973    1/1986
KR    20030003636 A    1/2003

OTHER PUBLICATIONS

Agro et al. "Retrograde Nasotracheal Intubation With a New Tracheal Tube: A Feasibility Study", British Journal of Anaesthesia, 2000, 84 (2), pp. 257-259, The Board of Management and Trustees of the British Journal of Anaesthesia 2000.

(Continued)

*Primary Examiner* — Lynne Anderson
*Assistant Examiner* — Bradley Philips
(74) *Attorney, Agent, or Firm* — Novak Druce Connolly Bove + Quigg LLP

(57) ABSTRACT

The present invention provides an intubation device including a nasal endotracheal tube having a proximal, relative to a person inserting the nasal endotracheal tube, end and a distal end; and an introducer including an elongated member having a proximal open end and a distal blunt end, the introducer proximal open end including a hollow mouth having sidewalls for receiving and holding the distal end of the endotracheal tube. The dilator/introducer is simply a tube, solid or hollow having a hollow proximal end that will hold a distal end of a nasal endotracheal tube in place. It will act as a dilator, and once the distal end of the endotracheal tube is past the nasopharynx and is visualized in the oropharynx, the "dilator" is removed and typically discarded. A method of use of the intubation device is also disclosed.

45 Claims, 10 Drawing Sheets

(56) References Cited

U.S. PATENT DOCUMENTS

| | | | |
|---|---|---|---|
| 4,655,214 A | 4/1987 | Linder | |
| 4,773,394 A * | 9/1988 | Reichstein et al. | 600/114 |
| 4,801,294 A | 1/1989 | Okada | |
| 4,819,619 A | 4/1989 | Augustine et al. | |
| 4,887,997 A | 12/1989 | Okada | |
| 5,259,377 A | 11/1993 | Schroeder | |
| 5,279,610 A | 1/1994 | Park et al. | |
| 5,323,771 A | 6/1994 | Fisher et al. | |
| 5,334,167 A | 8/1994 | Cocanower | |
| 5,339,805 A | 8/1994 | Parker | |
| 5,339,806 A | 8/1994 | Beaussant et al. | |
| 5,401,241 A | 3/1995 | Delany | |
| 5,692,506 A | 12/1997 | Linder | |
| 5,749,357 A | 5/1998 | Linder | |
| 5,791,341 A | 8/1998 | Bullard | |
| 5,803,080 A | 9/1998 | Freitag | |
| 6,382,209 B1 * | 5/2002 | Toye | 128/207.14 |
| 6,481,436 B1 | 11/2002 | Neame | |
| 6,637,435 B2 | 10/2003 | Ciaglia et al. | |
| 6,706,017 B1 | 3/2004 | Dulguerov | |
| 6,978,784 B2 | 12/2005 | Pekar | |
| RE39,508 E | 3/2007 | Parker | |
| 2004/0098013 A1 | 5/2004 | Ciaglia et al. | |
| 2004/0231675 A1 * | 11/2004 | Lyons | 128/207.18 |
| 2005/0177025 A1 | 8/2005 | Jaker et al. | |
| 2005/0183729 A1 | 8/2005 | Fischer, Jr. | |
| 2006/0173422 A1 * | 8/2006 | Reydel et al. | 604/271 |
| 2007/0073107 A1 | 3/2007 | Peartree et al. | |
| 2008/0078405 A1 * | 4/2008 | Crumback et al. | 128/207.15 |
| 2009/0320854 A1 * | 12/2009 | Cuevas et al. | 128/207.29 |

OTHER PUBLICATIONS

Elwood et al. "Nasotracheal Intubation A Randomized Trial of Two Methods", Anesthesiology, 2002, 96, pp. 51-53, 2002 American Society of Anesthesiologists, Inc. Lippincott Williams & Wilkins, Inc.

"Bard 14 fr Red Rubber Utility Catheter" Webpage printout from http://www.qualitymedicalsupplies.com/page/QMS/PROD/52-RC/277714 dated Apr. 1, 2008.

"Robinson-Nelaton Straight Red Rubber Catheter-Sterile" Webpage printout from http://www.southwestmedical.com/index.php?page_type=popus&popup-images&product_... dated Apr. 1, 2008.

* cited by examiner

ATRAUMATIC INTRODUCER FOR NASAL ENDOTRACHEAL TUBES AND ITS METHOD OF USE

CROSS REFERENCE TO RELATED APPLICATION

This application is a §371 National Stage Application of International Application No. PCT/U.S.2008/059946, filed on 10 Apr. 2008, claiming the priority of U.S. Provisional Application No. 60/911,168 filed on 11 Apr. 2007, incorporated herein by reference in its entirety.

FIELD OF THE INVENTION

The principal utility of the present invention relates to an introducer for nasal endotracheal tubes and its method of use in nasal intubation for throat, oral and maxillofacial surgery, or nasal intubation for patients in an intensive care unit for a few days or nasal intubation for patients operated on while awake.

BACKGROUND OF THE INVENTION

Surgery requiring general anesthesia for oral, maxillofacial and some throat procedures require the patient be intubated nasally so the surgeon has access to the respected surgical site.

One significant problem with nasal intubation is it is very difficult to pass the desired sized endotracheal tube through the nasal passage. The clinician usually has to use a smaller than desired endotracheal tube to pass through the nasal anatomy. The problem with this fact is the endotracheal tube will be too small to properly fit the larynx, and thus too large of an air leak will be present around the tube. Too large of an air leak around the endotracheal tube would result in insufficient pressure in the pulmonary tree, thus making it very difficult, if not impossible, to ventilate the patient. If the patient is not properly ventilated, it is difficult to maintain the appropriate saturation levels of oxygen and anesthetic gases.

Another problem with a nasal intubation is that the open beveled distal end of an endotracheal tube can traumatize the anatomy of the nasal passages and the tissue of the adenoids. Many times the nasal endotracheal tube will remove adenoidal tissue which can occlude the lumen of the nasal endotracheal tube and/or produce a bleed from the tissue in question.

A nasal endotracheal tube can also tunnel through and along the posterior wall of the nasopharynx which will also result in an occluded lumen of the endotracheal tube and may also produce a bleed or swelling of the tissue. The result of this wound could not become apparent until after surgery and could be life threatening. Blood and tissue may not make an occlusion of the nasal endotracheal tube apparent until well into a procedure when blood would clot within the tube. This would raise a patient's carbon dioxide level and lower their oxygen saturation level, which could also lead to morbidity and mortality. The nasal endotracheal tube can also damage the turbinate bones in the nasal passages. There have been documented cases of these turbinates being avulsed and even aspirated into the pulmonary tree. An avulsion of the middle turbinate can expose the floor of the cranial vault and can leak cerebral spinal fluid.

Bleeding from the pharyngeal region can also trigger a laryngospasm. This occurs when fluid (i.e. blood) makes contact with the vocal cords. If a patient is in a certain stage of anesthesia and protective reflexes are not intact then the vocal cords if stimulated by a fluid may spasm and close, thus losing the airway. This could result in death, or central nervous system damage. If blood is introduced into the pulmonary tree (i.e., aspirated) then a post-operative pneumonia may also develop.

An endotracheal tube may also may carry and introduce microbes from the nasal passages into the pulmonary tree. This may again lead to pneumonia.

The article Elwood et al., Nasotracheal Intubation, A Randomized Trial of Two Methods, Anesthesiology 2002:96; 51-3 discloses an evaluation of red rubber catheters as a guide to nasotracheal intubation. In the trial children presented for elective surgery were randomized to undergo red-rubber catheter-guided nasotracheal intubation or to have the nasotracheal tube alone inserted. The results were that age, weight, snoring history, and difficulty of intubation were not different between the groups. Obvious bleeding was lower using the red-rubber catheter technique, which took longer to perform.

SUMMARY OF THE INVENTION

The present invention is a dramatic improvement over the procedure of Elwood et al., Nasotracheal Intubation, A Randomized Trial of Two Methods, Anesthesiology 2002:96; 51-3.

The dilator/introducer permits the operator to better place the correct sized endotracheal tube due to its increasing, circumferential diameter. In particular, the dilator/introducer typically has a progressively tapered shape which is relatively narrower at its distal end (distal relative to the uses intubating a patient, and relatively wider at its proximal end. The increase in the circumference/perimeter aids the operator in incrementally dilating the nasal tissues such that an endotracheal tube, of sufficient outer diameter to properly fit the larynx, can be passed through the respective nasal anatomy. In contrast, the red rubber catheter generally has an outer diameter too small to dilate the tissues. Thus, a desired sized endotracheal tube may not be able to passed through the nasal anatomy in a safe and rapid manner. Moreover, dilating the nasal turbinates with the present introducer in an incremental fashion, and not by blunt dilation of the endotracheal tube coupled to the red rubber catheter, will lessen the chance of damaging or braking these cartilaginous structures.

Also, the present dilator/introducer can more quickly pass through the nasal anatomy and introduce the endotracheal tube into the oropharynx. The lack of relative stiffness of the red rubber catheter makes it necessary to advance it through the nasal passage in small increments and then pull it through. In contrast, the present introducer/dilator is sufficiently rigid to be pushed through in one or two strokes such that much less time elapses. Time is important, because at this phase of anesthesia and intubation, the patient is not breathing on his or her own and is not being supported by the operator.

Another advantage of the present dilator/introducer is that the distal, beveled end of the endotracheal tube is not bulging out from its respective proximal end. The distal end of the endotracheal tube is bulging through the proximal wall of the red rubber catheter such that it can still impact the anatomy and will slow the progression of the two tubes through the nasal anatomy.

Another advantage of preferred embodiments of the present dilator/introducer is that if one would want to pull the dilator and endotracheal tube in reverse back through the nose, the proximal flange of the red rubber catheter could evert and traumatize the nasal soft tissues and may impede the removal of the two devices. Preferably the dilator/introducer is stiff enough and has beveled or rounded edges of the outer circumference of its mouth such that it can removed in a smooth manner that is both safe and not time consuming.

Another advantage with the dilator/introducer over a red rubber catheter is that the operator will be better able to determine if the endotracheal tube that he or she has chosen will pass through the nasal anatomy. Since the dilator/introducer is less stiff than the endotracheal tube, it can help determine if the endotracheal tube will impinge that anatomy such that it will not pass through to the oropharynx safely. In other words, if the dilator/introducer becomes impinged and can not be moved through the nasal anatomy, one will not have to determine the same thing with the endotracheal tube which is much stiffer and thus could do damage, even when coupled with the red rubber catheter.

It is an object of the present invention to provide an atraumatic nasal endotracheal tube dilator/introducer for safe introduction of a nasal endotracheal tube.

The present invention provides an intubation device comprising:

a nasal endotracheal tube having a proximal end, relative to a person inserting the nasal endotracheal tube, and a distal end; and a dilator/introducer comprising an elongated member having a proximal open end and a distal blunt end, the dilator/introducer proximal open end comprising a hollow mouth having sidewalls for receiving and holding the distal end of the endotracheal tube, wherein a distal end portion of the dilator/introducer has tapered sidewalls, wherein the tapered sidewalls increase in effective diameter at least 10% from a first distal location to a first proximal location, wherein the first distal location is within 1 inch, for example, within 0.5 inches, or within 0.25 inches, of the distal end of the dilator/introducer, wherein the longitudinal distance from the first distal location to the first proximal location is at least 0.5 inches, and the tapered sidewalls increase in effective diameter at least 10% from the first proximal location distal location to a second proximal location which is more proximal than the first proximal location to the proximal end of the dilator/introducer, wherein the longitudinal distance from the first proximal location to the second proximal location is at least 0.5 inches.

The cavosurface, or outer and inner edges of the proximal end of the introducer can be rounded with no line angles or be beveled/chamfered.

The dilator/introducer is simply a tube, solid or hollow, having a hollow proximal end that will hold a distal end of a nasal endotracheal tube in place. The dilator/introducer typically has a progressive, tapering external diameter. The most distal end would have the smallest external diameter and would increase in size to the most proximal end which would have the largest external diameter.

Typically the distal blunt end of the dilator/introducer is beveled or rounded.

The dilator/introducer has sidewalls defining a tapered longitudinal contour wherein the angle of taper, represented by a tangent at respective points along the dilator/introducer outer surface, progressively decreases from the distal end to the proximal end. Also, typically the dilator introducer has an absence of step changes in contour over 10 degrees, typically an absence of step changes in contour over 30 degrees, relative to a longitudinal axis of the introducer.

It will act as a dilator, and once the distal end of the endotracheal tube is visualized in the oropharynx, the "dilator" is removed and typically discarded.

An embodiment of the atraumatic nasal endotracheal tube dilator/introducer includes a hollow proximal end, a cylindrical body, and a closed distal end. The hollow proximal end allows the coupling of the open distal end of the nasal endotracheal tube within it. The closed distal end of the dilator/introducer facilitates its passage and the passage of the endotracheal tube through the nasal anatomy and past the posterior wall of nasopharynx and adenoidal tissue.

The distal end is blunt to reduce the risk of trauma to tissue. By a blunt distal end it is meant the distal end lacks a sharp point and lacks sharp edges which can traumatize tissue. Typically, the distal end forms a convex surface or hemispherical surface. The distal end may form a frustoconical surface, or a tapered surface, if there are no sharp edges which can traumatize tissue. Generally the distal end is closed. However, a opening axially centered in the distal end is permitted if it does not have sharp edges which can traumatize tissue.

The dilator/introducer will prevent the open distal end of a nasal endotracheal tube from avulsing nasal and adenoidal tissue and tunneling through the posterior wall of the nasopharynx. The dilator/introducer may also act as a soft tissue dilator to help the correct sized endotracheal tube transverse swollen nasopharyngeal tissues on its path to the trachea. It will also lessen or eliminate damage to the turbinate bones. Once the endotracheal tube is visualized in the oropharynx, the dilator/introducer is pulled free from it and discarded.

DETAILED DESCRIPTION OF THE PREFERRED EMBODIMENT

Figure 1:
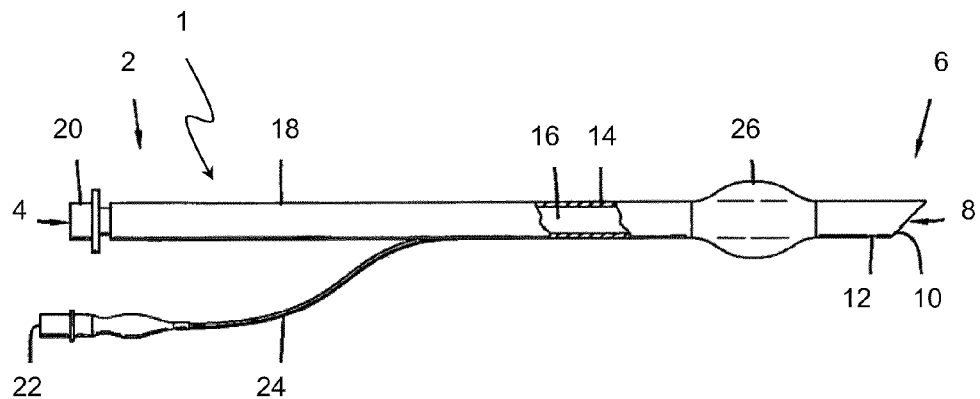
FIG. 1 is a schematic illustration of an exemplary endotracheal tube of the prior art.

The present invention provides an intubation device comprising:

a nasal endotracheal tube having a proximal end, relative to a person inserting the nasal endotracheal tube, and a distal end; and a dilator/introducer comprising an elongated member having a proximal open end and a distal blunt end, the dilator/introducer proximal open end comprising a hollow mouth having sidewalls for receiving and holding the distal end of the endotracheal tube, wherein a distal end portion of the dilator/introducer has tapered sidewalls, wherein the tapered sidewalls increase in effective diameter at least 10% from a first distal location to a first proximal location, wherein the first distal location is within 1 inch, for example, within 0.5 inches, or within 0.25 inches, of the distal end of the dilator/introducer, wherein the longitudinal distance from the first distal location to the first proximal location is at least 0.5 inches, for example, 1 to 6 inches or 2 to 4 inches, and the tapered sidewalls increase in effective diameter at least 10% from the first proximal location to a second proximal location which is more proximal than the first proximal location to the proximal end of the dilator/introducer, wherein the longitudinal distance from the first proximal location to the second proximal location is at least 0.5 inches, for example 1 to 12 inches or 2 to 8 inches.

More typically, the tapered sidewalls increase in effective diameter at least 15% from the first distal location to the first proximal location, wherein the first distal location is within 0.25 inches of the distal end of the dilator/introducer, wherein the longitudinal distance from the first distal location to the first proximal location is at least 1 inch, for example, 1 to 6 inches or 2 to 4 inches, and wherein the tapered sidewalls increase in effective diameter at least 15% from the first proximal location to the second proximal location, wherein the longitudinal distance from the first proximal location to the second proximal location is at least 1 inch, e.g., 1 to 12 inches or 2 to 8 inches.

Still more typically, the tapered sidewalls increase in effective diameter at least 15% from the first distal location to the first proximal location, wherein the first distal location is within 1 inch of the distal end of the dilator/introducer, wherein the longitudinal distance from the first distal location to the first proximal location is at least 10%, or at least 20%, of the length of the dilator/introducer, and wherein the tapered sidewalls increase in effective diameter at least 15% from the first proximal location to the second proximal location, wherein the longitudinal distance from the first proximal location to the second proximal location is at least 10%, or at least 20%, of the length of the dilator/introducer, wherein the dilator/introducer has a length of at least 5 inches, for example 5 to 24 inches.

If desired, the tapered sidewalls increase in effective diameter, for example, 5 to 200% or 5 to 100% or 10 to 50% or 10 to 20% or 25 to 40% from the first distal location to the first proximal location. If desired, the tapered sidewalls increase in effective diameter, for example, 5 to 200% or 5 to 100% or 10 to 50% or 10 to 20% or 25 to 40% from the first proximal location to the second proximal location. If desired, the first distal location is within 2 inches, or within 1 inch, e.g., 0.1 inches or 0.25 inches or 0.5 inches, of the distal end of the dilator/introducer. If desired, the longitudinal distance from the first distal location to the first proximal location is 10% to 60% or 20% to 40% of the length of the dilator/introducer. If desired, the longitudinal distance from the first proximal location to the second proximal location is 10% to 60%, or 20% to 40%, of the length of the dilator/introducer. Typical lengths of the dilator/introducer include at least 5 inches, or 5 to 30 inches, or 5 to 24 inches, or other lengths as disclosed elsewhere in this specification.

By effective diameter ($d_{eff}$) is meant the diameter of a circular cross-section having the same area as the cross-section of the dilator/introducer regardless of its shape. It is calculated according to equation (1) derived as follows:

$$A = \tfrac{1}{4}(\pi d^2)$$

$$4A/\pi = d^2$$

$$(4A/\pi)^{0.5} = d_{eff} \qquad (1)$$

where d=diameter of a circle (inches, mm)

$d_{eff}$=effective diameter (inches, mm)

A=cross-sectional area section of the dilator/introducer (inches$^2$, mm$^2$).

However, for these non-circular shapes, typically the narrowest width across the cross-section is 20 to 100%, or 40 to 90%, of the widest width across the cross section.

The present invention also provides an intubation device comprising:

a nasal endotracheal tube having a proximal end, relative to a person inserting the nasal endotracheal tube, and a distal end; and an introducer comprising an elongated member having a proximal open end and a distal blunt end, the introducer proximal open end comprising a hollow mouth having sidewalls for receiving and holding the distal end of the endotracheal tube, wherein the proximal open end defines the only opening of the introducer.

The present invention also provides a nasal endotracheal tube introducer comprising:

an elongated member having a first open end and a second closed end, the first open end being selected from the group consisting of a hollow mouth section of greater inner diameter than an outer diameter of a nasal endotracheal tube being inserted thereinto and a hollow mouth section sufficiently elastic to expand to a greater diameter than the nasal endotracheal tube being inserted thereinto, the elongated member having a length for insertion thereof past the nasopharyngeal region into the oropharyngeal region, wherein the introducer has an outer diameter of 12 french to 46 french and the mouth section has an inner diameter of 3 mm to 11.5 mm.

Figure 2:
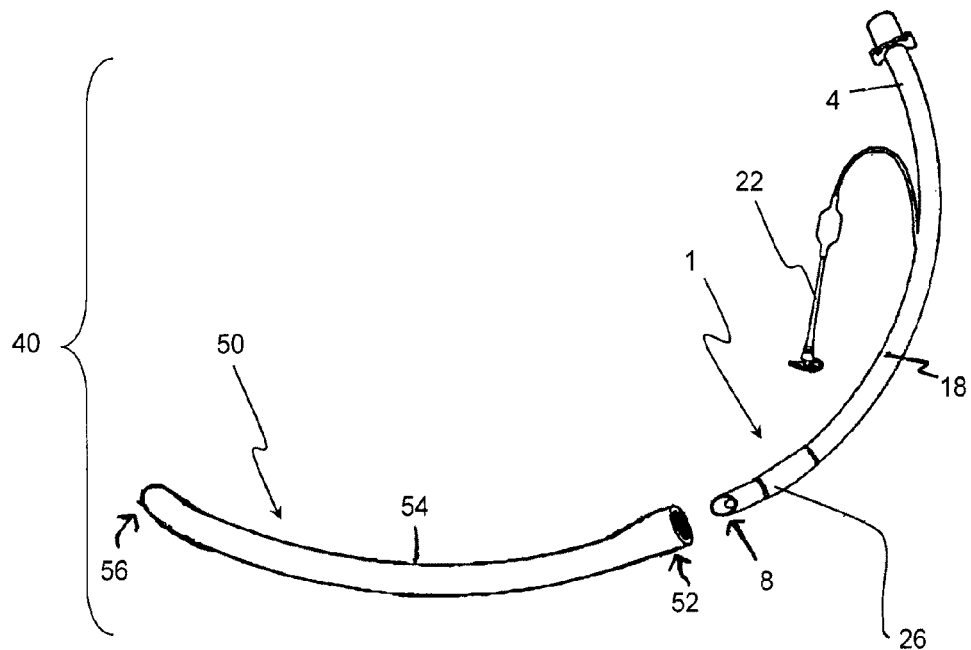
FIG. 2 is an illustration of the endotracheal tube of FIG. 1 and a dilator/introducer of the present invention.

FIG. 1 shows an exemplary hollow nasal endotracheal tube 1, comprising an endotracheal tube tubular member 18 having an endotracheal tube lumen 16 for gas flow, defined by a cylindrical endotracheal tube wall 14, extending between a proximal opening at a proximal endotracheal tube end 2 and a distal opening 8 at a distal endotracheal tube end 6 of endotracheal tube tubular member 18. Cylindrical wall 14 of endotracheal tube 2 may have an outer diameter less than the inner diameter of dilator/introducer 50 (FIG. 2). If the dilator/introducer 50 is sufficiently flexible then the inner diameter D1 of the dilator/introducer 50 may be the same or slightly smaller than the outer diameter of the distal end of the endotracheal tube 1 and expands to snugly fit the distal end of the endotracheal tube 1.

Inflatable cuff or balloon 26 circumscribes endotracheal tube tubular member 18 adjacent distal endotracheal tube end 6 and communicates with an inflation port 22 via inflation tubing 24. Proximal end 1 of tubular member 9 is adapted to receive a connector piece 20 into which tubing (not shown) for gas flow to a patient may be attached.

Distal endotracheal tube end 6 of endotracheal tube tubular member 18 terminates in a beveled tip whose shorter terminus 10 defines the anterior aspect of endotracheal tube 1. A Murphy eye 12 is fashioned into cylindrical wall 14 of endotracheal tube tubular member 18 adjacent distal end 6 to provide an alternative pathways for gas flow to a patient should distal opening 8 of endotracheal tube tubular member 18 become occluded. Depending on the flexibility of material used, the endotracheal tube 1 may be straight or naturally curved to nasal-pharyngeal anatomy.

FIG. 2 shows an embodiment of a nasal intubation system 40 of the present invention including a nasal endotracheal tube 1 having its distal end 8 aligned for being inserted into an embodiment of a nasal endotracheal tube dilator/introducer 50 of the present invention. The dilator/introducer 50 of this and other embodiments of the present invention preferably has a length sufficient for extending the proximal end of the introducer outside the nares when the distal end of the dilator/introducer is out of the mouth while the nasal endotracheal tube is inserted within a patient. The dilator/introducer 50 of this and other embodiments of the present invention is bendable but sufficiently stiff to be self supporting. By self supporting it is meant that the dilator/introducer if held up from a lower end does not significantly bend due to mere gravity. Moreover, it has shape memory so that if a force is applied to bend the dilator/introducer away from its original longitudinal axis then when the force is removed the dilator/introducer returns to its original shape. It is typically a sufficiently stiff elastomeric polymer.

Moreover, the dilator/introducer 50 tapered longitudinal contour of this and other embodiments of the present invention progressively decreases from the distal end to the proximal end and has an absence of step changes in contour over 10 degrees relative to a longitudinal axis of the introducer.

Figure 3:
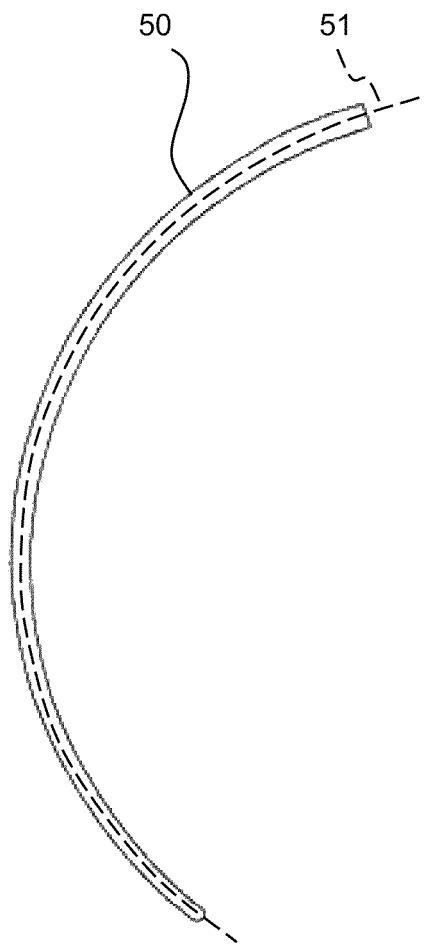
FIG. 3 is an illustration of the dilator/introducer of FIG. 2.

FIG. 3 is an illustration of the dilator/introducer 50 of FIG. 2. The dilator/introducer 50 has sidewalls defining a tapered longitudinal contour which progressively decreases from the distal end to the proximal end and has an absence of step changes in contour over 10 degrees, typically less than 5 degrees, relative to a longitudinal axis 51 of the dilator/introducer 50.

Figure 3A:
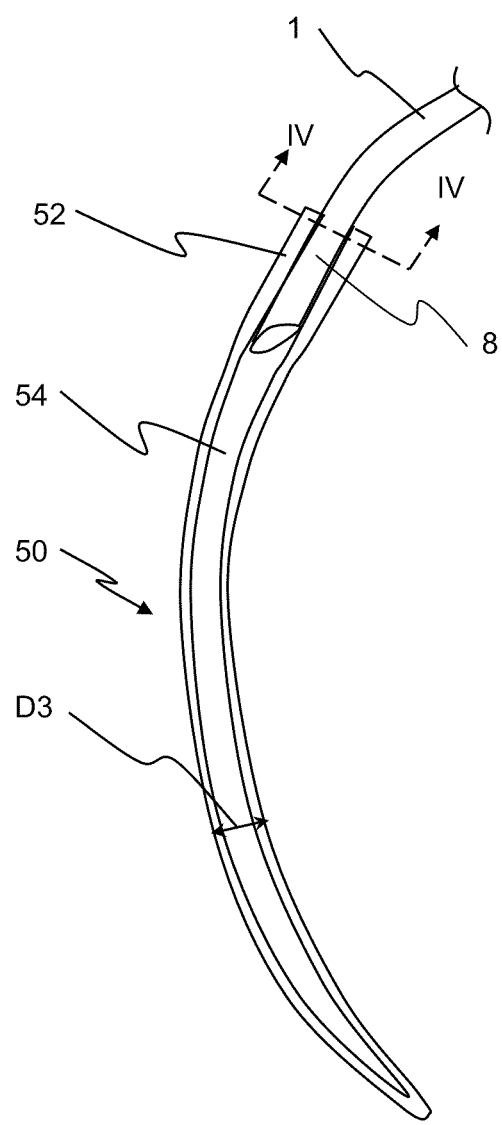
FIG. 3A is a cross-sectional view of a distal end of the endotracheal tube of FIG. 1 inserted into the proximal end of the dilator/introducer of FIG. 2.

FIG. 3A is a cross-sectional view of a distal end of the endotracheal tube of FIG. 1 inserted into the proximal end of the dilator/introducer 50 of FIG. 2.

The nasal endotracheal tube 1 of FIG. 2 has an extended inflation port 22 as compared to that of FIG. 1.

Nasal endotracheal tube dilator/introducer 50 includes a hollow proximal end 52, a cylindrical body 54, and a closed distal end 56. The hollow proximal end 52 allows the coupling of the open distal end 8 of the nasal endotracheal tube 1 within it.

The closed distal end 56 of the dilator/introducer 50 facilitates its passage and the passage of the endotracheal tube 1 through the nasal anatomy, and past the posterior wall of nasopharyngeal and adenoidal tissue.

The dilator/introducer 50 will prevent the open distal end 8 of the nasal endotracheal tube 1 from avulsing nasal and adenoidal tissue and tunneling through the posterior wall of the nasopharynx.

The dilator/introducer 50 may also act as a soft tissue dilator to help the correct sized endotracheal tube 1 transverse swollen nasopharyngeal tissues on its path to the trachea. It will also lessen or eliminate damage to the turbinate bones. Once the endotracheal tube 1 is visualized in the oropharynx, the dilator/introducer 50 is pulled free from it and is discarded.

Figure 4:
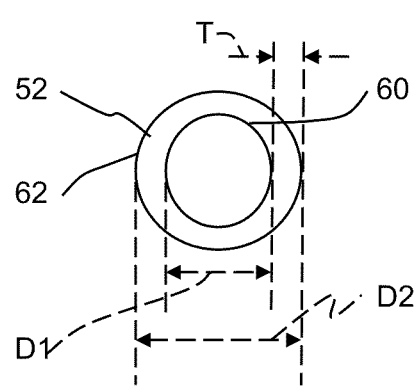
FIG. 4 is an end view of the proximal end of the dilator/introducer of FIG. 2 along cross-section IV-IV.

FIG. 4 shows the proximal end 52 of the dilator/introducer 50 has inner walls 60 having an inner diameter D1 and outer walls having an outer diameter D2. The inner diameter D1 being sufficiently sized to insert the distal end 8 of the endotracheal tube 1 to fit snug within it and releasably held within it by friction. If the dilator/introducer 50 is sufficiently rigid then the inner diameter D1 of the dilator/introducer 50 may be slightly larger than the outer diameter of the distal end of the endotracheal tube 1. However, typically the inner diameter D1 of the dilator/introducer 50 is the same or slightly smaller than the outer diameter of the distal end of the endotracheal tube 1 and expands to snugly fit the distal end of the endotracheal tube 1.

For example, the inner diameter D1 of the proximal end 52 of the dilator/introducer 50 may be smaller than the outer diameter of the distal end 8 of the nasal endotracheal tube 1 and expand to fit the distal end 8 of the nasal endotracheal tube 1. The cylindrical body 54 of the endotracheal tube introducer 50 typically has an outer diameter D2 of 12 french (4.0 mm) to 46 french (15.3 mm) and the mouth section 52 has an inner diameter D1 of 3 mm to 11.5 mm. The introducer has a sufficient length for insertion thereof past the nasopharyngeal region into the oropharyngeal region. Most typically the introducer has a length of 5 to 12 inches or 5 to 18 inches.

Figure 5:
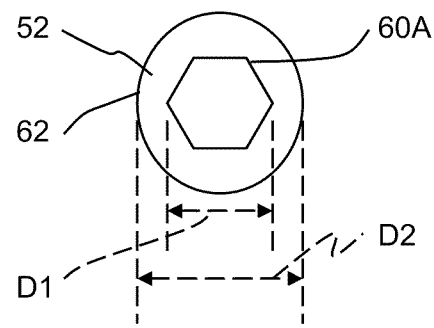
FIG. 5 is an end view of the proximal end of a hexagonal variation of the dilator/introducer of FIG. 2.

If desired, the inner walls or outer walls or both the inner and outer walls may have a non-cylindrical oval or polygonal perimeter. For example, FIG. 5 shows an embodiment of a proximal end 52 of the dilator/introducer 54 modified to have hexagonal inner walls 60A having an inner diameter D4 and outer walls 62 having the outer diameter D2.

The outer diameter D2 of the proximal end 52 of the dilator/introducer 50 in use may be greater than the outer diameter D3 of the cylindrical body 54 as shown in FIG. 2.

Figure 6:
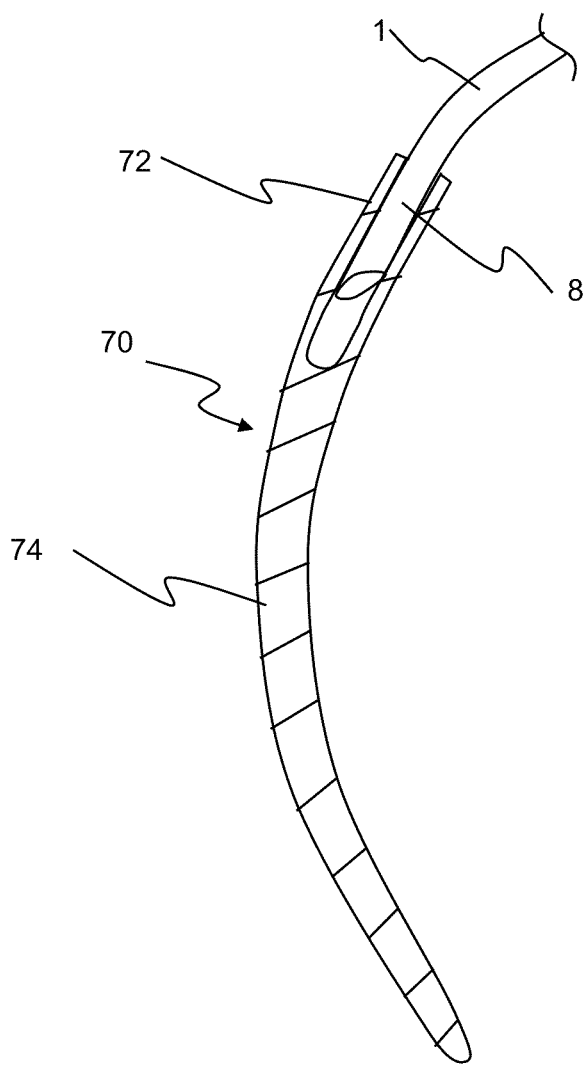
FIG. 6 is a cross-sectional view of a distal end of the endotracheal tube of FIG. 1 inserted into the proximal end of a variation of the dilator/introducer of FIG. 2.

However, the present invention also encompasses embodiments wherein the proximal end and the cylindrical body of the dilator/introducer have the same outer diameter over at least a substantial portion of its length. For example, FIG. 6 shows a dilator/introducer 70 having a proximal end 72 and cylindrical body 74 having the same outer diameter in its portion immediately adjacent to the proximal end 72 and at least a substantial portion of the length of the cylindrical body 74. Preferably the cylindrical body 74 is tapered at least at its distal-most portion.

Figure 7:
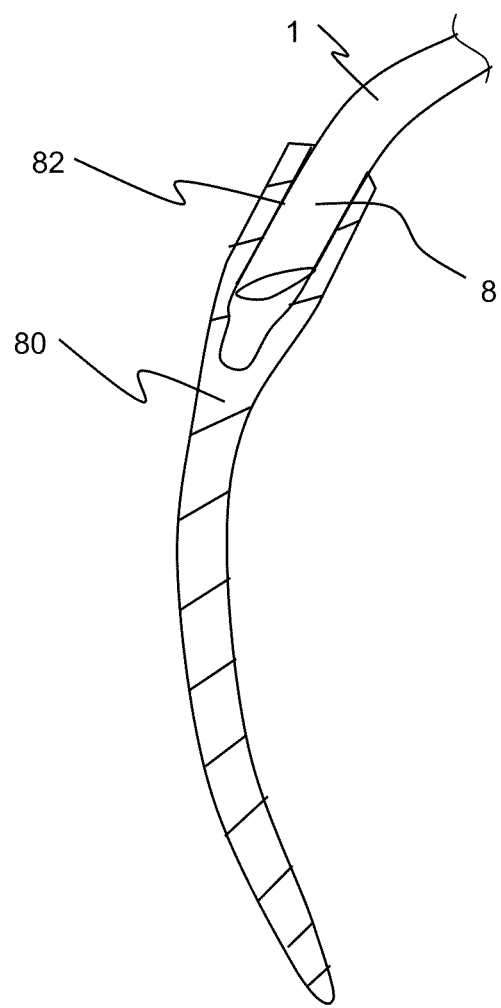
FIG. 7 is a cross-sectional view of a distal end of the endotracheal tube of FIG. 1 inserted into the proximal end of another variation of the dilator/introducer of FIG. 2.

Another option is for the outer diameter D2 of the proximal end 52 of the dilator/introducer 50 at rest to be the same as the outer diameter D3 of the cylindrical body 54 prior to inserting the distal end 8 into the proximal end 52, but for the outer diameter D2 of the proximal end 52 of the dilator/introducer 50 to expand upon inserting the distal end 8 of the nasal endotracheal tube 1 into the proximal end 52 of the dilator/introducer 50 as shown in FIG. 7.

The endotracheal tube dilator/introducer cylindrical body 54 may be of the same outer circumference for its entire length or may taper to have a narrower diameter as it approaches the most distal end point.

The proximal end 52 of the dilator/introducer 50 is open to allow the distal end 8 of the endotracheal tube 1 to fit snug within it. The rest of the dilator/introducer may be hollow, as shown in FIG. 3 for the dilator/introducer 50, or solid, as shown in FIGS. 6 and 7, depending on the type of material used as well its durometer and wall thickness.

FIG. 6 shows a cross-section of a dilator/introducer 70 having an open proximal end 72 and a solid remainder. For example, the endotracheal tube introducer may be solid until the proximal-most 10 to 50 mm.

FIG. 7 shows a cross-section of a dilator/introducer 80 of the present invention in which the proximal end 82 of the dilator/introducer 80 is open to allow the distal end 8 of the endotracheal tube 1 to fit snug within it.

Also, depending on the flexibility of material used, the dilator/introducer may be straight or naturally curved to nasal-pharyngeal anatomy.

The distal end 56 of the dilator/introducer 50 is blunt to reduce the risk of trauma to tissue. By a blunt distal end it is meant the distal end lacks a sharp point and lacks sharp edges which can traumatize tissue. The distal end 56 of the dilator/introducer 50 may be rounded, slightly bulbous, or may terminate in a small surface area such as a bullet ending with a small round nose at its apex. Typically, the distal end forms a convex surface or hemispherical surface.

Figure 8:
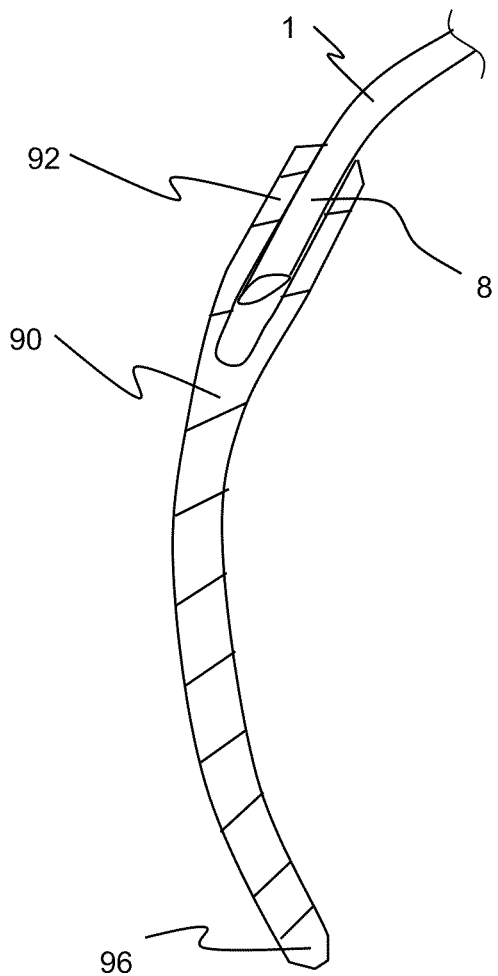
FIG. 8 is a cross-sectional view of a distal end of the endotracheal tube of FIG. 1 inserted into the proximal end of another variation of the dilator/introducer of FIG. 2.
Figure 9:
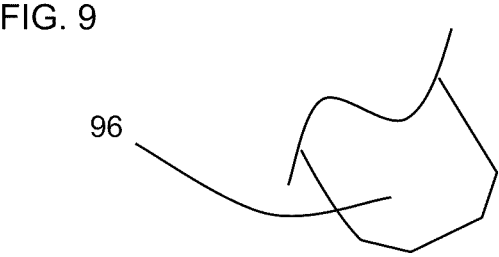
FIG. 9 is an enlarged view of a distal end of the embodiment of FIG. 8.

FIGS. 8 and 9 show another embodiment of a dilator/introducer 90 the present invention in which the distal end forms a frustoconical surface which is chamfered, beveled or tapered, with no sharp edges which can traumatize tissue.

Figure 10:
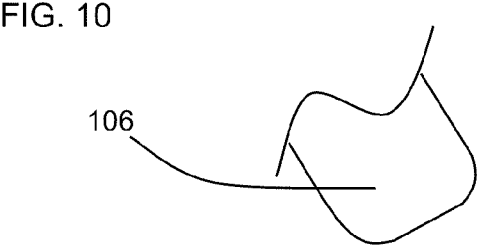
FIG. 10 is an enlarged view of a distal end of a variation of the embodiment of FIG. 8.

FIG. 10 shows a modified distal end 106 of an introducer having a flat end with rounded sides.

Figure 11:
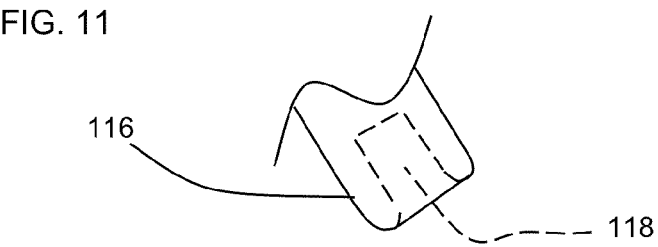
FIG. 11 is an enlarged view of a distal end of another variation of the embodiment of FIG. 8.

Generally the distal end is closed. However, an axially centered opening in the distal end is permitted if it does not have sharp edges which can traumatize tissue. FIG. 11 shows a modified distal end 116 of an introducer having an open distal end with rounded sides.

FIG. 2 shows the deflated balloon or cuff 26 of the cuffed endotracheal tube 1. The cuff 26 is inflated after an adult is intubated to complete the seal of the pulmonary tree to properly ventilate the pulmonary tree. The cuff 26 is deflated before the patient is extubated.

Figure 12:
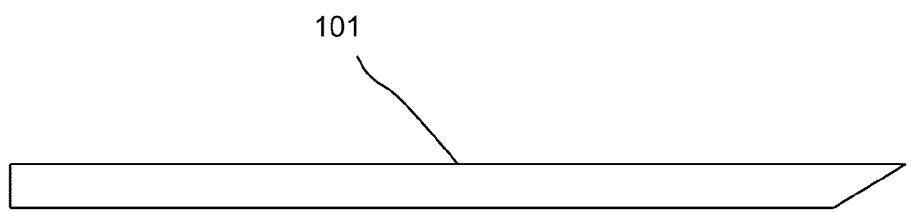
FIG. 12 is a schematic illustration of another exemplary endotracheal tube of the prior art.

An uncuffed hollow endotracheal tube 101 (FIG. 12) has no cuff and is used for pediatric patients, because one wants a small leak to keep pressures lower in their larynx. Depending on the flexibility of material used, the endotracheal tube 101 may be straight or naturally curved to nasal-pharyngeal anatomy.

Also depending on the flexibility of material used, the dilator/introducer may be straight or naturally curved to nasal-pharyngeal anatomy.

When using cuffed endotracheal tube 1 the director/dilator 50 would attach distal to the cuff 26 so as not to damage the cuff 26 when it is separated from the endotracheal tube 1.

Figure 13:
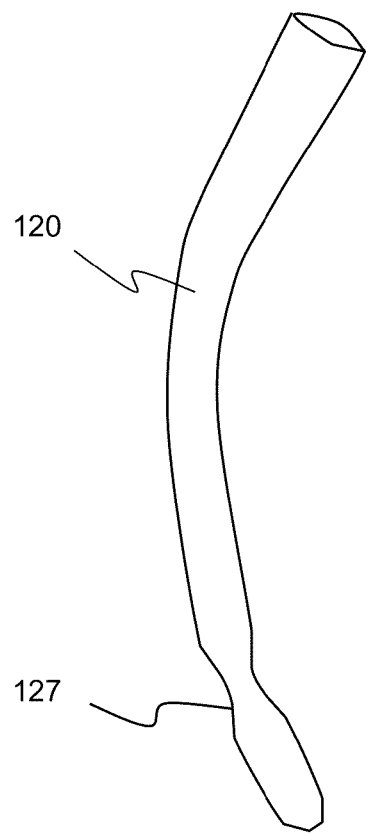
FIG. 13 is a perspective view of another variation of the dilator/introducer of FIG. 2 modified to have a circumferential indentation.

There may be a circumferential indentation or a circumferential raised rib at some point along the body of the dilator/introducer to facilitate pulling it through to the desired location and separating it from the endotracheal tube 1 at the appropriate time. FIG. 13 shows a circumferential indentation 127 at a point along the body of a dilator/introducer 120 to facilitate pulling it through to the desired location and separating it from the endotracheal tube 1 at the appropriate time.

Figure 14:
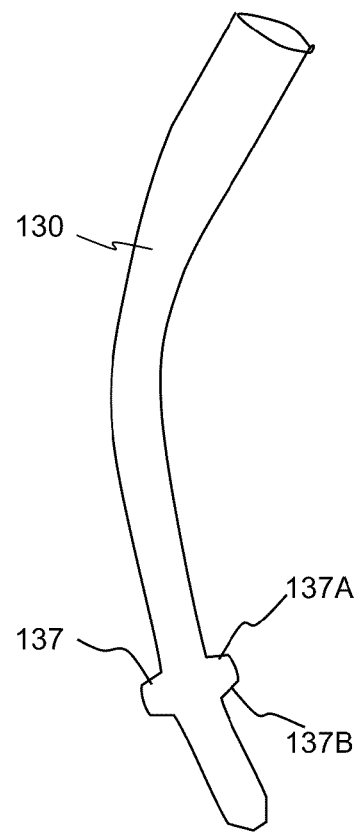
FIG. 14 is a perspective view of another variation of the dilator/introducer of FIG. 2 modified to have a circumferential protrusion (rib).

FIG. 14 shows a circumferential raised rib 137 at a point along the body of a dilator/introducer 130 to facilitate pulling it through to the desired location and separating it from the endotracheal tube 1 at the appropriate time. However, the raised rib has tapered proximal and distal sides 137 A, B, respectively, to facilitate intubation.

Typically the dilator/introducers of the present invention would be made of a medically approved polymer, such as polyisoprene, latex, rubber, polyvinyl chloride, silicone rubber, or any other suitable material that does or would meet FDA guidelines. Typical materials are flexible polymers. However, if desired the materials may be relatively rigid. Silicone rubber is a synthetic elastomer made from a cross-linked polymer reinforced with silica. Preferably it is latex-free. In contrast, red rubber catheters contain latex.

Figure 15:
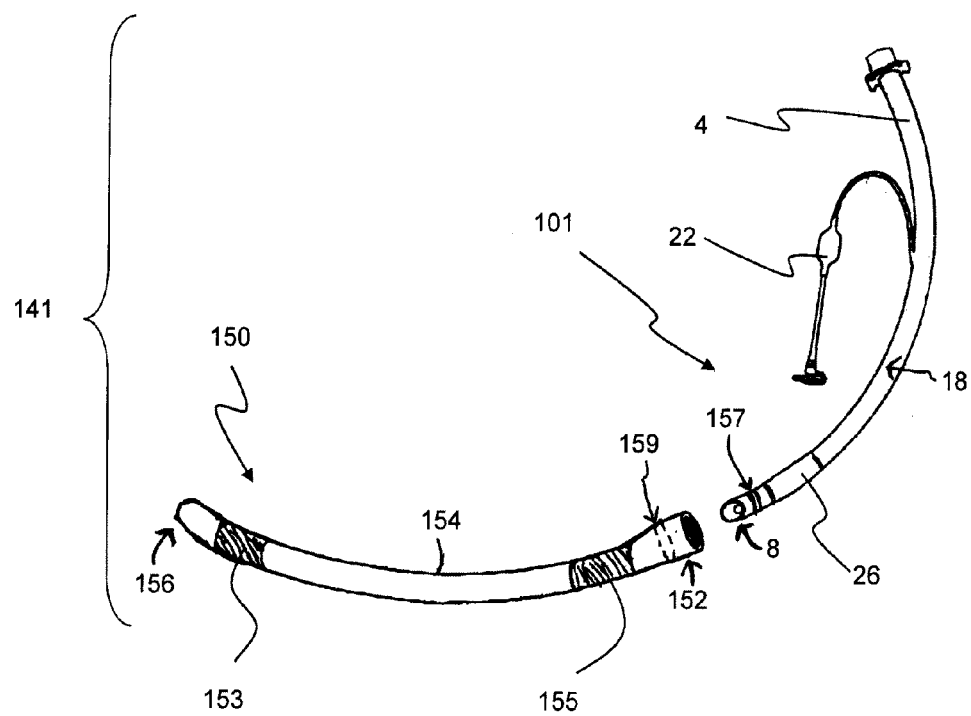
FIG. 15 is an illustration of a modified version of the endotracheal tube of FIG. 2 and a modified version of the dilator/introducer of FIG. 2.

FIG. 15 shows another embodiment of a system 141 of the present invention including a nasal endotracheal tube dilator/introducer 150 of the present invention. The dilator/introducer 150 includes a hollow proximal end 152, a cylindrical body 154, and a closed distal end 156. The hollow proximal end 152 allows the coupling of the open distal end 8 of the nasal endotracheal tube 101 within it. The dilator/introducer 150 also has regions 153, 155 for grasping. Also, the endotracheal tube 101 has an external circumferential groove 157 which can mate with a raised internal circumferential rib 159 of the dilator/introducer 150.

The dilator/introducer of the present invention preferably has a progressive increase in its diameter as it approaches the most proximal end which attaches to the endotracheal tube. It will dilate the tissues and give the operator a much greater ability to use the desired size endotracheal tube.

The dilator/introducer is typically completely smooth along its entire outer surface, thus greatly reducing the chance of tissue trauma.

The dilator/introducer's most proximal end (relative to the person doing the intubation to the patient) is relatively stiff and has a sufficient wall thickness for making it a safe and predictable device for intubating a patient even if it has to be pulled backwards through the nose during the intubation procedure or operation.

Preferably the dilator/introducer has a rounded (or beveled/chamfered) surface around its most proximal end to minimize the risk of trauma, irritation or bleeding and to help make a smooth passage for both the introducer and the endotracheal tube.

Figure 16:
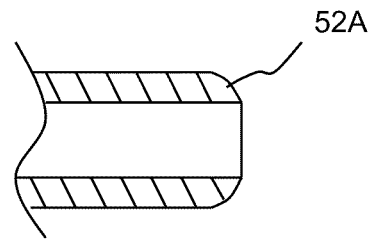
FIG. 16 shows a proximal end of the dilator/introducer of FIG. 2 modified to be rounded.

FIG. 16 shows a proximal end 52A of the dilator/introducer 54 of FIG. 2 modified to be rounded.

Figure 17:
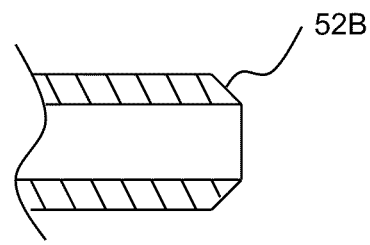
FIG. 17 shows a proximal end of the dilator/introducer of FIG. 2 modified to be beveled.

FIG. 17 shows a proximal end 52B of the dilator/introducer 54 of FIG. 2 modified to be beveled.

It is pliable or supple enough such that it can make the bend around the posterior aspect of the soft palate with relative ease and can also be coupled and removed from the distal aspect of the endotracheal tube with ease. However, preferably, the dilator/introducer has a structure and stiffness which facilitates being pushed through the nasal anatomy as opposed to being pulled through. A problem with pulling it through is that one could traumatize the posterior aspect of the soft palate by placing contact and friction pressure on it.

Preferably, the dilator/introducer has a sufficiently large diameter and wall thickness such that it will not collapse in on itself when pushed through the nasal anatomy. The entire nasal endotracheal tube introduction is preferably accomplished with a pushing motion to avoid pull on the soft palate when this invention is utilized. However, if necessary the dilator/introducer may be pushed and pulled during an intubation or operation. For example, the dilator/introducer could be initially pushed into the nose and then, after its distal end is out of the mouth and the proximal end is in the oropharynx, it could be pulled.

Preferably to avoid being caught in the nasal anatomy this invention employs a gradual increase in the diameter of the introducer until it mates with the endotracheal tube where the two blend their diameters such that there is a smooth transition in size and no abrupt step change in diameter at the point of mating as well as along the introducer. Therefore, the chance of the tubes being caught in the nasal anatomy is greatly diminished.

Thus, the device is designed to avoid collapsing when being pushed through a nasal passage. Size, wall thickness, material type (e.g., its fiber cross linkage), durometer, shape (design), radius of curvature and mass may contribute to avoiding collapsing when being pushed through a nasal passage. A typical hardness range is a Shore A hardness of 35 to 85 durometer as measured by ASTM D2240 type A scale. The open proximal end of the dilator/introducer has a wall thickness T (FIG. 4) of about 0.04 to 0.1 inches (not counting the potentially thinner wall created at the edge of the dilator/introducer due to the optional rounding off or bevelling/chamfering at the edge).

TABLE 1 lists typical ranges for dimensions of the dilator/introducer.

TABLE 1

| Parameter | Broad | Typical | More Typical |
|---|---|---|---|
| Length of dilator/introducer | 5 to 24 inches | 5 to 18 inches | 7 to 12 inches |
| Outer diameter or effective diameter of dilator/introducer if hollow* | 10 french to 46 french | 12 french to 40 french | 18 french to 34 french |
| Inner diameter or effective diameter of dilator/introducer if hollow at rest** | 1 mm to 11.5 mm | 3 mm to 11.5 mm | 4 mm to 9 mm |
| Outer diameter or effective diameter of dilator/introducer if solid* | 10 french to 50 french | 12 french to 46 french | 18 french to 36 french |
| Inner diameter or effective diameter of mouth section of dilator/introducer if solid at rest*** | 3 to 11.5 mm | 4.5 to 10 mm | 6 to 9 mm |
| Wall thickness, inches | 0.025 to 0.11 inches | 0.04 to 0.09 inches | 0.045 to 0.085 inches |
| Hardness, Shore A durometer, ASTM D-2240, hollow embodiments | about 30 to 80 | about 35 to 70 | about 40 to 60 |
| Hardness, Shore A durometer, ASTM D-2240, solid embodiments | about 20 to 60 | about 30 to 50 | about 35 to 50 |

*Outer Diameter of at least 90% of the dilator/introducer, with the proviso that the distal end, e.g., distal-most 5% to 10% of the length of the dilator/introducer, may have a diameter in this range or smaller. Outer diameter preferably tapers to narrow in going from the proximal end to the distal end.
**Inner Diameter of at least 90% of the hollow portion of the dilator/introducer, at rest, i.e., in an non-stretched state, with the proviso that the distal end, e.g., distal-most 5% to 10% of the length of the hollow portion of the dilator/introducer, may have a diameter in this range or smaller.
***Inner Diameter of at least 90% of the mouth portion of the dilator/introducer, at rest, i.e., in an non-stretched state, with the proviso that the distal end, e.g., distal-most 5% to 10% of the length of the mouth portion of the dilator/introducer, may have a diameter in this range or smaller.

The ranges for diameter permit a tube where a portion of the tube is solid and another portion is hollow. For example, the distal half or three quarters could be solid with the remainder hollow or the proximal half or three quarters could be solid (but for the hollow mouth) with the remainder hollow. For example, the dilator/introducer may be solid until the proximal-most 10 to 50 mm.

Moreover, the inner and outer diameters do not necessarily include the distal-most tip (e.g., distal-most half inch) which could be smaller than the disclosed diameter ranges since it could come to a point, such at the top of a hemispherical dome.

Some typical non-limiting examples of suitable parameters are as follows:

Size 14 French introducer/dilator may have a distal end inner diameter of 0.05 inches, an outer diameter of 0.106 inches and a wall thickness of 0.028 inches, a proximal end inner diameter of 0.091 inches and an outer diameter of 0.185 inches and a wall thickness of 0.047 inches, and a length of 12 inches and a taper of 0.089 inches, made of a polyvinyl chloride material of 65 durometer. Another suitable material is MEDIPRENE thermoplastic elastomer having a Shore A 42 durometer hardness or equivalent.

Size 20 French dilator/introducer may have a distal end inner diameter of 0.091 inches, an outer diameter of 0.185 inches and a wall thickness of 0.047 inches, a proximal end inner diameter of 0.130 inches and an outer diameter of 0.264 inches and a wall thickness of 0.067 inches, and a length of 12 inches and a taper of 0.189 inches, made of a polyvinyl chloride material of Shore A hardness of 65 durometer. Another suitable material is MEDIPRENE thermoplastic elastomer or its equivalent having a Shore A hardness, ASTM D-2240, of 42 durometer.

Size 26 French dilator/introducer may have a distal end inner diameter of 0.130 inches, an outer diameter of 0.264 inches and a wall thickness of 0.067 inches, a proximal end inner diameter of 0.169 inches and an outer diameter of 0.343 inches and a wall thickness of 0.087 inches, and a length of 15 inches and a taper of 0.151 inches, made of a polyvinyl chloride material of Shore A hardness of 65 durometer. Another suitable material is MEDIPRENE thermoplastic elastomer having an ASTM D-2240 Shore A 42 durometer hardness or equivalent.

Size 32 French dilator/introducer may have a distal end inner diameter of 0.169 inches, an outer diameter of 0.343 inches and a wall thickness of 0.087 inches, a proximal end inner diameter of 0.209 inches and an outer diameter of 0.421 inches and a wall thickness of 0.106 inches, and a length of 15 inches and a taper of 0.0149 inches, made of a polyvinyl chloride material of Shore A hardness of 65 durometer. Another suitable material is MEDIPRENE thermoplastic elastomer having a Shore A 42 durometer hardness or equivalent.

The dilator/introducer is sufficiently stiff to be self supporting but sufficiently flexible to be able to bend during intubation. Stiffness and bendability will be a result of selection of material and thickness. For example, a typical dilator/introducer of the present invention would be significantly stiffer than a red rubber catheter. For example, here is a hypothetical comparison of thickness according to a three point bending test of the following:

(1) a hypothetical dilator/introducer of the present invention made of natural rubber and having an outer diameter (OD) of 0.375 inches and a wall thickness (t) of 0.06 inches and an inside diameter (ID) of 0.255 inches with (2) a hypothetical red rubber catheter assumed to be made of the same natural rubber and having an outer diameter (OD) of 0.140 inches and a wall thickness (t) of 0.040 inches and an inside diameter (ID) of 0.06 inches.

Figure 18:
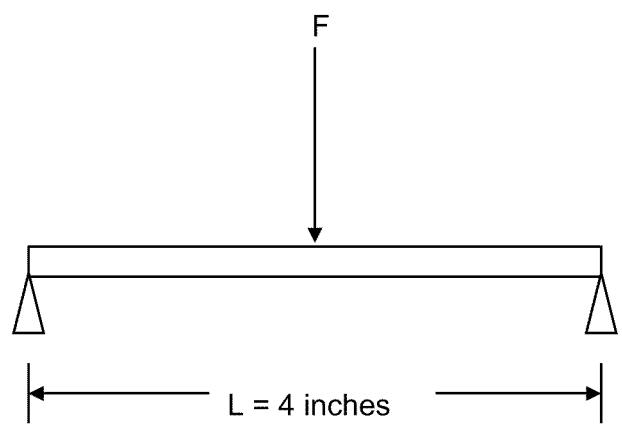
FIG. 18 schematically shows a three-point bending test apparatus.

Assuming a 4 inch simply supported beam as in FIG. 18, and assuming the material is a natural rubber having a Young's elastic modulus (also known as a "linear modulus" which is a small strain modulus) of 190 pounds-force/square inch, results in the following equations (4)-(7) for moment of inertia "I":

$$I_{inventive\ tube} = \pi/64(d_o^4 - d_i^4) \quad (4)$$

$$I_{inventive\ tube} = \pi/64((0.375)^4 - (0.255)^4) = 7.6317 \times 10^{-4} \text{ in.}^4 \quad (5)$$

$$I_{red\ tube} = \pi/64(d_o^4 - d_i^4) \quad (6)$$

$$I_{red\ tube} = \pi/64((0.140)^4 - (0.06)^4) = 1.8221 \times 10^{-4} \text{ in.}^4 \quad (7)$$

Stiffness of the hypothetical simply supported beam with a central load "F" is calculated according to the following equation 8.

$$K = (48 \times E \times I)/L^3 \quad (8)$$

Where E is Young's modulus of elastic rubber
I is moment of inertia
L is the length of the rod
Deflection under the load is calculated as follows by equation (9):

$$\text{Deflection} = F/k = FL^3/(48 \times E \times I) \quad (9)$$

Thus, the ratio of the stiffness of the hypothetical inventive tube can be compared to the typical red rubber tube is as follows in equations (10 and (11):

$$k_{inventive\ tube}/k_{red\ tube} = (((48 \times E \times I_{inventive\ tube})/L^3)/(48 \times E \times I_{red\ tube})/L^3) \quad (10)$$

$$k_{inventive\ tube}/k_{red\ tube} = 42/1 \quad (11)$$

Thus, although the same material was used for the hypothetical red rubber catheter and the dilator/introducer of the present invention, the red rubber catheter has wall and diameter dimensions to be much more flexible than the present dilator/introducer. In contrast, the dimensions of the dilator/introducer are selected to be much stiffer. This softness of the red rubber catheter is required because of the normal use of a red rubber catheter, namely, as a urinary catheter inserted through the urethra to evacuate urine from the bladder. Likewise due to its normal use, a red rubber catheter has a side wall hole adjacent its distal end to provide a passage for urine when evacuating the bladder.

Use of the Atraumatic Dilator/Introducer

Prior to a nasal intubation the correct sized nasal endotracheal tube 1 (FIG. 1) is selected. Next the appropriate sized dilator/introducer 50 is chosen to couple correctly with the endotracheal tube 1 (FIG. 2, FIG. 3), in which case the anesthesiologist inserts the distal end 8 of the endotracheal tube 1 snugly into the proximal open end 52 of the director 50. Alternatively, a nasal endotracheal tube 1 may come prepackaged with the dilator/introducer 50 already mated to the nasal endotracheal tube 1.

Intubation would start with the operator inserting the dilator/introducer 50 into the patient's nose and advancing it manually until it became visualized in the oropharynx. At this point, the operator would grasp the dilator/introducer 50 with forceps, such as McGill forceps, and pull the dilator/introducer 50 on through until the endotracheal tube 1 is visible. A grasping area 153 on the dilator/introducer 50 may be marked by the above mentioned rib or indentation. This procedure may still involve pushing of the endotracheal tube 1 from its proximal end 8 as one pulls from its distal end 4. Once the endotracheal tube is visible, the operator needs to grasp the endotracheal tube 1 just proximal to the interface of the dilator/introducer 50 with his forceps and pull on the director with his other hand so as to separate the two from each other. For, example, if the dilator/introducer has a proximal grasping area 155 (FIG. 15), this area would be grasped by the forceps prior to separation. Once this is accomplished, the endotracheal tube is free from those above mentioned tissues and the intubation can proceed in a normal fashion.

Therefore, as compared to existing methods of nasal intubation there are significant advantages to this invention.

First, the dilator/introducer's tapering form will allow the clinician to select the most appropriate sized endotracheal tube to properly fit the larynx. The dilation of the tissues in the nasal passages will allow the larger endotracheal tube to pass by these compressed tissues which could not be accomplished unless these tissues were severely traumatized. A major advantage to this invention is the ability to use the correct sized endotracheal tube so the clinician may properly ventilate the patient.

Second, the dilator/introducer's rounded distal end 56 would greatly minimize or eliminate trauma and bleeding found with the use of the endotracheal tube 1 alone. Bleeding and trauma to the nasal passages, nasopharynx, adenoids and all other associated mucosa may result in the following intraoperative and postoperative complications. First, blood that would run down the posterior wall of the pharynx and make contact with the vocal cords may result in a laryngospasm.

A laryngospasm, prior to the passage of the endotracheal tube will result in the closure of the vocal cords, resulting in a loss of the airway. If the laryngospasm is not quickly corrected via positive pressure or paralytic medication, the patient will eventually asphyxiate and die. A second complication from bleeding is the possibility of blood passing the vocal cords, no laryngospasm occurring, and becoming introduced into the pulmonary tree. This may result in a postoperative pneumonia which could also eventually result in the death of the patient.

Another complication from bleeding is the introduction of blood and/or adenoidal or mucosal tissue into the lumen of the endotracheal tube 1. These body materials may eventually clot and dry and thus compromising the flow dynamics of the endotracheal tube 1. This may require the extubation and reintubation of the patient in the middle of a procedure which is a risky procedure at that time and place. This could also lead to hypoxia and possible death.

Still another complication of the traditional method of intubation is the fact that the endotracheal tube 1 will deliver microbes to the pulmonary tree by those microbes in the nasal passage attaching to the distal aspect of the endotracheal tube (both extraluminal and intraluminal) and then shedding into the pulmonary anatomy.

Another complication of a traditional nasal endotracheal intubation is that the areas traumatized may become infected. Infection may become serious enough to require antibiotics and possibly extending the hospital stay of the patient. This trauma will also result in discomfort to the patient that could last for some period of time.

A person of ordinary skill in the art can see the dilator/introducer of the present invention isolates the open distal end of an nasal endotracheal tube from the above tissues and thus greatly reduces the likelihood of trauma to this region. Preferably the dilator/introducer of the present invention does not provide a through passage. Thus, mucus or other body fluids or tissue are kept away from the open end of the nasal endotracheal tube. The dilator/introducer of the present invention also totally eliminates the chance of the nasal endotracheal tube's lumen being occluded from tissue in the above mentioned anatomical area.

Having now fully described the invention, it will be apparent to one of ordinary skill in the art that many changes and modifications can be made without departing from the spirit or scope of the invention as herein described.

I claim:

1. A device comprising:
a nasal endotracheal tube having a for being closer to a person inserting the nasal endotracheal tube, and a distal end; and
a dilator/introducer comprising an elongated member having a proximal open end and a distal blunt end, wherein the distal end of the elongated member does not have an opening and is unopenable, wherein the distal end of the elongated member comprises a distal-most end wall, and wherein the proximal end of the elongated member comprises a proximal-most side edge, the proximal-most side edge defining the only opening for receiving the endotracheal tube;
the elongated member proximal open end comprising mouth having sidewalls for receiving the distal end of the endotracheal tube only through the proximal-most side edge and holding the distal end of the endotracheal tube,
wherein a distal end portion of the dilator/introducer has tapered sidewalls and comprises the distal end of the elongated member,
wherein the tapered sidewalls increase in effective diameter at least 10% from a first distal location to a first proximal location,
wherein the first distal location is within 1 inch of the distal end of the dilator/introducer,
wherein the longitudinal distance from the first distal location to the first proximal location is at least 0.5 inches, and
wherein the tapered sidewalls increase in effective diameter at least 10% from the first proximal location to a second proximal location which is more proximal than the first proximal location to the proximal end of the dilator/introducer,
wherein the longitudinal distance from the first proximal location to the second proximal location is at least 0.5 inches and wherein the hollow mouth is at the proximal-most side edge of the dilator/introducer, wherein the hollow mouth sidewalls for receiving and holding the distal end of the endotracheal tube has a continuous transverse perimeter along the entire perimeter for surrounding the distal end of the endotracheal tube.

2. The device of claim 1,
wherein the tapered sidewalls increase in effective diameter at least 15% from the first distal location to the second proximal location,
wherein the first distal location is within 0.5 inches of the distal end of the dilator/introducer,
wherein the longitudinal distance from the first distal location to the first proximal location is at least 1 inch, and
wherein the tapered sidewalls increase in effective diameter at least 15% from the first proximal location to the second proximal location,
wherein the longitudinal distance from the first proximal location to the second proximal location is at least 1 inch.

3. The device of claim 1,
wherein the tapered sidewalls increase in effective diameter at least 15% from the first distal location to the second proximal location,
wherein the first distal location is within 0.25 inches of the distal end of the dilator/introducer,
wherein the longitudinal distance from the first distal location to the first proximal location is at least 5% of the length of the dilator/introducer, and
the tapered sidewalls increase in effective diameter at least 15% from the first proximal location distal location to the second proximal location,
wherein the longitudinal distance from the first proximal location to the second proximal location is at least 5% of the length of the dilator/introducer.

4. The device of claim 1, wherein the dilator/introducer is bendable but sufficiently stiff to be self supporting; the dilator/introducer having closed sidewalls extending from the distal end to the proximal end.

5. The device of claim 1, wherein the tapered longitudinal contour progressively decreases from the distal end to the proximal end and has an absence of step changes in contour over 30 degrees relative to a longitudinal axis of the introducer.

6. The device of claim 1, wherein the hollow mouth is sufficiently elastic to expand upon insertion of the distal end of the nasal endotracheal tube thereinto.

7. The device of claim 1, wherein the mouth section has a greater outer diameter than the remainder of the dilator/introducer.

8. The device of claim 1, wherein the dilator/introducer has a length of 5 to 18 inches.

9. The device of claim 1, wherein the dilator/introducer has an outer diameter of 12 french to 46 french from the first proximal location to the proximal end of the dilator/introducer and the mouth section has an inner diameter of 3 mm to 11.5 mm.

10. The device of claim 8, wherein the dilator/introducer is solid until the proximal-most 10 to 50 mm.

11. The device of claim 1, wherein the dilator/introducer is hollow and self-supporting and has a wall thickness of about 0.02 inches to 0.14 inches and a Shore A durometer rating of about 30 to about 80.

12. The device of claim 1, wherein the dilator/introducer is hollow and self-supporting and has a wall thickness of about 0.067 inches to 0.106 inches and a Shore A durometer rating of about 40 to about 60.

13. The device of claim 1, wherein the dilator/introducer is solid, but for its mouth, and self-supporting and has an outer diameter of 12 french to 46 french and a Shore A durometer rating of about 20 to about 60.

14. The device of claim 1, wherein the dilator/introducer is solid, but for its mouth, and self-supporting and has an outer diameter of 12 french to 46 french of at least 90% of the dilator/introducer, with the proviso that the distal end of the length of the introducer, has a diameter in this range or smaller; and a Shore A durometer rating of about 30 to about 50.

15. The device of claim 1, wherein the dilator/introducer has at least one member of the group consisting of a distal grasping area for grasping with forceps and a proximal grasping area for grasping with forceps.

16. The device of claim 1, wherein the endotracheal tube has an external circumferential groove which can mate with a raised internal circumferential rib of the dilator/introducer.

17. The device of claim 1, wherein the dilator/introducer has a tapered longitudinal contour, wherein the diameter of the introducer increases from the distal end to the proximal end, and the dilator/introducer has an absence of step changes in longitudinal contour over 30 degrees relative to a longitudinal axis of the introducer.

18. The device of claim 1, wherein the dilator/introducer proximal-most end is rounded or beveled.

19. A method for using the device of claim 1, comprising:
providing the dilator/introducer with a distal end of a nasal endotracheal tube inserted into the proximal end, relative to a person inserting the nasal endotracheal tube, of the introducer;
inserting the dilator/introducer into a patient's nose and advancing the introducer manually until the introducer is visualized in the oropharynx;
grasping the dilator/introducer and advancing the introducer on through until the endotracheal tube is visible;
when the endotracheal tube is visible, grasping the endotracheal tube just proximal to its interface of the dilator/introducer and pulling on the introducer to separate the endotracheal tube from the dilator/introducer.

20. The device of claim 1,
wherein the proximal open end defines the only opening of the dilator/introducer.

21. The device of claim 20, wherein the dilator/introducer has an outer diameter of 12 french to 46 french and the mouth section has an inner diameter of 3 mm to 11.5 mm.

22. The device of claim 20, wherein the introducer has a length of 5 to 12 inches.

23. The device of claim 20, wherein the introducer is solid until the proximal-most 10 to 50 mm.

24. The device of claim 20, wherein the introducer is hollow.

25. The device of claim 20, wherein the elongated member has grasping portions.

26. The device of claim 20, wherein the dilator/introducer has at least one member of the group consisting of a distal grasping area for grasping with forceps and a proximal grasping area for grasping with forceps.

27. The device of claim 20, wherein the proximal-most end of the dilator introducer is the proximal end of the elongated member and the distal-most end of the introducer is the distal end of the elongated member.

28. The device of claim 20, wherein the endotracheal tube has an external circumferential groove which can mate with a raised internal circumferential rib of the dilator/introducer.

29. The device of claim 20, wherein the endotracheal tube has an external circumferential groove which can mate with a raised internal circumferential rib of the dilator/introducer.

30. The device of claim 20, wherein the dilator/introducer is hollow and self-supporting.

31. The device of claim 1,
wherein the only open end of the dilator/introducer is the proximal open end
the elongated member having a length of 5 to 24 inches from the first end to the second end,
wherein the introducer has an outer diameter of 12 french to 46 french and the mouth section has an inner diameter of 3 mm to 11.5 mm.

32. The device of claim 31, wherein the introducer is hollow and self-supporting.

33. The device of claim 31, wherein the dilator/introducer is self-supporting and has a length of 7 to 18 inches from the distal end to the hollow proximal end.

34. The device of claim 33, wherein a distal three quarters of the dilator/introducer is solid with the hollow mouth at the proximal end.

35. The device of claim 33, wherein the dilator/introducer consists of a tube having a progressive, tapering external effective diameter, the tube being solid or hollow.

36. The device of claim 31, wherein the distal end of the introducer is a hemispherical or convex end wall.

37. The device of claim 31, wherein the hollow mouth sidewalls are selected from the group consisting of hollow mouth sidewalls of greater inner diameter than an outer diameter of nasal endotracheal tube being inserted thereinto and hollow mouth sidewalls sufficiently elastic to expand to a greater diameter than the nasal endotracheal tube being inserted longitudinally thereinto.

38. The device of claim 1, wherein the dilator/introducer consists of a tube having a progressive, tapering external effective diameter, the tube being solid or hollow.

39. The device of claim 1, wherein the dilator/introducer is self-supporting and has a naturally curved longitudinal axis forming an arc.

40. The device of claim 1, wherein the endotracheal tube has a Murphy eye and inflatable cuff and the dilator/introducer proximal open end hollow mouth having sidewalls for receiving and holding the distal end of the endotracheal tube at the proximal end of the dilator/introducer to attach distal to the cuff to not cover the cuff.

41. The device of claim 35, wherein the dilator/introducer is self-supporting and has a length of 7 to 18 inches from the distal end to the hollow proximal end.

42. The device of claim 35, wherein the distal three quarters of the dilator/introducer is solid with the hollow mouth at the proximal end.

43. A method for using the nasal endotracheal tube introducer of claim 31, comprising:
inserting the introducer into a patient's nose and advancing the introducer manually until the introducer is visualized in the oropharynx; grasping the introducer after the introducer is visualized.

44. The device of claim 1, wherein the distal end of the introducer is a hemispherical or convex end wall.

45. The device of claim 20, wherein the distal end of the introducer is a hemispherical or convex end wall.

* * * * *

UNITED STATES PATENT AND TRADEMARK OFFICE
CERTIFICATE OF CORRECTION

| | | |
|---|---|---|
| PATENT NO. | : 8,561,605 B2 | Page 1 of 1 |
| APPLICATION NO. | : 12/530668 | |
| DATED | : October 22, 2013 | |
| INVENTOR(S) | : John J. Davis | |

It is certified that error appears in the above-identified patent and that said Letters Patent is hereby corrected as shown below:

In the Claims

Claim 1, Column 15, Line 7 should read: "a nasal endotracheal tube having [[a]] for being closer to a"

Claim 1, Column 15, Line 20 should read: "a hollow mouth having sidewalls for..."

Signed and Sealed this
Sixth Day of May, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,561,605 B2 | Page 1 of 1 |
| APPLICATION NO. | : 12/530668 | |
| DATED | : October 22, 2013 | |
| INVENTOR(S) | : John J. Davis | |

It is certified that error appears in the above-identified patent and that said Letters Patent is hereby corrected as shown below:

In the Claims

Claim 1, Column 15, Lines 7-9 should read: "a nasal endotracheal tube having a proximal end for being closer to a person inserting the nasal endotracheal tube, and a distal end; and"

Claim 1, Column 15, Line 20 should read: "a hollow mouth having sidewalls for..."

This certificate supersedes the Certificate of Correction issued May 6, 2014.

Signed and Sealed this
Seventeenth Day of February, 2015

Michelle K. Lee
*Deputy Director of the United States Patent and Trademark Office*